US005728383A

United States Patent [19]
Johnson et al.

[11] Patent Number: 5,728,383

[45] **Date of Patent: *Mar. 17, 1998**

[54] TREATMENT OF TUMORS OF THE CENTRAL NERVOUS SYSTEM WITH IMMUNOTOXINS

[75] Inventors: Virginia Johnson, College Park; Richard J. Youle, Chevy Chase, both of Md.

[73] Assignee: The United States of America as represented by the Secretary of the Department of Health and Human Services, Washington, D.C.

[ * ] Notice: The term of this patent shall not extend beyond the expiration date of Pat. No. 5,352,447.

[21] Appl. No.: 258,712

[22] Filed: Jun. 13, 1994

Related U.S. Application Data

[63] Continuation of Ser. No. 925,417, Aug. 10, 1992, Pat. No. 5,352,447, which is a continuation of Ser. No. 401,412, Sep. 1, 1989, abandoned, which is a continuation-in-part of Ser. No. 301,376, Jan. 25, 1989, Pat. No. 5,208,021, which is a division of Ser. No. 236,225, Aug. 25, 1988, abandoned, which is a continuation-in-part of Ser. No. 105,172, Oct. 5, 1987, abandoned.

[51] Int. Cl.$^6$ .................................................. A61K 39/395
[52] U.S. Cl. .................. 424/183.1; 424/832; 424/194.1; 424/195.11; 514/8; 514/12; 514/21; 530/391.7; 530/394; 530/380; 530/388.1; 530/388.2; 530/388.22; 530/387.7; 530/388.8; 530/363

[58] Field of Search ................................ 424/183.1, 832, 424/194.1, 195.11; 514/8, 12, 21; 530/391.7, 394, 380, 388.1, 388.2, 388.22, 387.7, 388.8, 363

[56] References Cited

U.S. PATENT DOCUMENTS

| | | |
|---|---|---|
| 4,482,483 | 11/1984 | Curry et al. . |
| 4,894,443 | 1/1990 | Greenfield et al. . |
| 5,045,451 | 9/1991 | Uhr et al. . |
| 5,208,021 | 5/1993 | Johnson et al. . |
| 5,352,447 | 10/1994 | Johnson et al. . |

OTHER PUBLICATIONS

U.S. Army Medical Res. Institute of Infectious Diseases pp. 95–96 Annual Progress Report (1981).
Greenfield et al. Science Magazine (1987) 238, pp. 536–539.
Laird et al, J. of Virology, (1976), 19, pp. 220–227.
O'Keefe et al (1985) J. Biol. Chem. 260(2) : 932–937.
Colombatti et al (1986) J. Biol. Chem. 261 (7):3030–3035 (Mar. 5 issue).
Laird et al (1976) J. Virology 19(1): 220–227.
Zovickian et al (1987) J. Neurosurg. 66 :850–861 (Jun. issue).
Roitt (1991) "Essential Immunology", Blackwell Scientific Publications, Oxford, pp. 65–68 & 74.
Lazar et al (1988) Molec. Cell. Biol. 8(3): 1247–1252.
Souza et al (1995) Proc. Nat'l Acad Sci. 92 :959–963.
Trowbridge et al (1981) Nature 294:171–172.
Youle et al (1986) J. Immunol. 136(1):93–98 (Jan. 1 issue).
Johnson et al (1989) J. Neurosurg. 70:240–248.
Youle et al (1988), in "Immunotoxins" (A.E. Frankel, ed.), Kluwer Academic Publishers, pp. 113–122.
Youle (1991) Sem. Cell Biol. 2 : 39–45.
Winkelman et al (1987) Arch. Neurol. 44: 526–531 (May issue).
Gregoriadis et al (1993) Trends in Biotech 11:440–442.
Jain (1994) Scientific American (Jul. issue) : pp. 58–65.
Waldman (1991) Science 252 : 1657–1662.
Boch et al (1993) Immunology Today 14(9): 421–425.
Goldstein et al (1986) Scientific American 255: 74–83.
Riedel et al (1990) Proc. Nat'l. Acad Sci. 87 : 5051–5055.
Esworthy et al (1984) J. Biol. Chem. 259(18) : 11496–11504.

*Primary Examiner*—Paula K. Hutzell
*Assistant Examiner*—Heather A. Bakalyar
*Attorney, Agent, or Firm*—Klarquist, Sparkman, Campbell, Leigh & Whinston

[57] ABSTRACT

Potent and specific immunotoxins are prepared by conjugation of moieties binding to receptors on the surface of tumor cells to a mutant diphtheria toxin having A-chain translocation activity, but lacking membrane-binding activity. The immunotoxins are used to treat primary tumors of neurologic origin, metastatic tumors of small cell lung carcinoma or breast carcinoma origin, leptomeningeal leukemia and leptomeningeal carcinomatosis. The preferred route of administration of the immunotoxin is to a compartment of the body containing cerebrospinal fluid.

12 Claims, 8 Drawing Sheets

Protein Synthesis (% Control) vs Toxin Concentration (M)

FIG. 8B

Protein Synthesis (% Control) vs Toxin Concentration (M)

TREATMENT OF TUMORS OF THE CENTRAL NERVOUS SYSTEM WITH IMMUNOTOXINS

This application is a continuation of application Ser. No. 07/925,417, filed on Aug. 10, 1992, now U.S. Pat. No. 5,352,447, which is a continuation of application Ser. No. 07/401,412, filed on Sep. 1, 1989, now abandoned, which is a continuation-in-part of application Ser. No. 07/301,376, filed on Jan. 25, 1989, now U.S. Pat. No. 5,208,021, which is a divisional of application Ser. No. 07/236,225, filed on Aug. 25, 1988, now abandoned, which is a continuation-in-part of application Ser. No. 07/105,172, filed on Oct. 5, 1987, now abandoned.

The invention claimed in the instant application relates to treatment of malignancies and to use of immunotoxins as an adjunct to chemotherapy for malignancies occurring in any part of the body to prevent development of metastatic lesions in the body which are usually not responsive to conventional chemotherapeutic agents. The use of the invention in treatment of central nervous system malignancies is particularly valuable.

BACKGROUND OF THE INVENTION

The use of systemic chemotherapy and radiation therapy for treatment of malignancies has failed to effectively alter the progress of malignant tumors of the central nervous system. The fatal outcome resulting from malignancies such as prostatic and mammary malignancies is often due to inability of current chemotherapy to effectively reach malignant growths in the central nervous system.

Thus use of cytotoxic products in the treatment of cancer is well known. The difficulties associated with such treatment are also well known. Of these difficulties, the lack of cancer-specific cytotoxicity has received considerable attention, albeit resolution of these difficulties has met with marginal success. Cytotoxic products kill normal cells as well as cancer cells. Such non-specificity results in a number of undesirable side effects for patients undergoing cancer chemotherapy with cytotoxic products, including nausea, vomiting, diarrhea, hemorrhagic gastroenteritis, and hepatic and renal damage. Due to normal cell toxicity, the therapeutic dosage of cytotoxic products has been limited such that cancerous cells are not killed to a sufficient level that subsequently prevents or delays new cancerous growth.

Current approaches to cancer chemotherapy and other immunological therapies focus on the use of cell-specific antibodies bonded to toxins in order to kill specific population of cancer cells. Immunotoxins (protein toxins chemically linked to tumor-specific monoclonal antibodies or other ligands) offer potential advantages over more conventional forms of treatment by having higher tumor specificity. Ideally, immunotoxins should discriminate to a high degree between target and non-target cells. The critical point, then, is the development of immunotoxins that are highly toxic for specific populations of cells.

Monoclonal antibodies linked to toxic proteins (immunotoxins) can selectively kill some tumor cells in vitro and in vivo. However, reagents that combine the full potency of the native toxins with the high degree of cell-type selectivity of monoclonal antibodies have not previously been designed.

Immunotoxins may be particularly efficacious for the treatment of neoplastic disease confined to compartments such as the peritoneum or intrathecal space. Direct delivery into the compartment avoids complications associated with systemic delivery and produces relatively high local concentrations, thereby achieving greater therapeutic effects. The cerebrospinal fluid compartment may be amenable to this type of compartmentalized immunotoxin treatment. Zovickian and Youle, *J Neurosurg*, in press, examined the therapeutic effect of a monoclonal antibody-ricin immunotoxin delivered directly into the CSF compartment in a guinea pig model of lepameningeal neoplasia. The immunotoxin therapy extended survival, corresponding to a 2–5 log kill of tumor cells, without detectable toxicity.

Protein toxins used in the constructions of immunotoxins have an A and a B subunit. The A subunit catalyzes the inactivation of protein synthesis, resulting ultimately in cell death. The B subunit has two functions: it is responsible for toxin binding to the cell surface, and it facilitates the translocation of the A chain across the membrane and into the cytosol, where the A chain acts to kill cells.

Previously, two general types of immunotoxins have been used. Immunotoxins made with the complete toxin molecule, both A and B chains, have the complication of non-specific killing mediated by the toxin B chain binding site. This can be avoided by eliminating the B chain and linking only the A chain to the antibody. However, A chain immunotoxins, although more specific, are much less toxic to tumor cells. The B chain, in addition to having a binding function, also has an entry function, which facilitates the translocation of the A chain across the membrane and into the cytosol. Since A-chain immunotoxins lack the entry function of the B chain, they are less toxic than their intact toxin counterparts containing the complete B chain. An ideal toxin for immunotoxin construction would contain the A chain enzymatic function and the B chain translocation function, but not the B chain binding function.

Two heretofore inseparable activities on one polypeptide chain of diphtheria toxin and ricin account for the failure to construct optimal reagents. The B-chains facilitate entry of the A-chain to the cytosol, allowing immunotoxins to kill target cells efficiently and bind to receptors present on most cells, imparting immunotoxins with a great degree of non-target-cell toxicity.

Some toxins have been modified to produce a suitable immunotoxin. The two best known are ricin and diphtheria toxin. Antibodies which bind cell surface antigens have been linked to diphtheria toxin and ricin, forming a new pharmacologic class of cell type-specific toxins. Ricin and diphtheria toxin are 60,000 to 65,000 dalton proteins with two subunits: the A-chain inhibits protein synthesis when in the cytosol, and the B-chain binds cell surface receptors and facilitates passage of the A subunit into the cytosol. Two types of antibody-toxin conjugates (immunotoxins) have been shown to kill antigen-positive cells in vitro. Immunotoxins made by binding only the toxin A subunit to an antibody have little non-target cell toxicity, but are often only minimally toxic to antigen-positive cells. Another type of immunotoxin is made by linking the whole toxin, A and B subunits, to the antibody and blocking the binding of the B subunit to prevent toxicity to non-target cells. For ricin, the non-target cell binding and killing can be blocked by adding lactose to the culture media or by steric restraint imposed by linking ricin to the antibody. Intact ricin immunotoxins may have only 30- to 100- fold selectivity between antigen-positive and negative cells, but they are highly toxic, and the best reagents can specifically kill a great many target cells.

Intact ricin and ricin A-chain immunotoxins have been found to deplete allogenic bone marrow of T cells, which can cause graft-versus-host diseases (GVHD), or to deplete autologous marrows of tumor cells.

Diphtheria toxin is composed of two disulfide-linked subunits: the 21,000 dalton A-chain inhibits protein synthesis by catalyzing the ADP-riboxylation of elongation factor 2, and the 37,000-dalton B-chain binds cell surface receptors and facilitate transport of the A-chain to the cytosol. A single molecule of either a diphtheria toxin A-chain or a ricin A-chain in the cytosol is sufficient to kill a cell. The combination of these three activities, binding, translocation, and catalysis, produces the extreme potency of these proteins. The cell surface-binding domain and the phosphate-binding site are located within the carboxyl-terminal 8-kDa cyanogen bromide peptide of the B-chain. Close to the C-terminus region of the B-chain are several hydrophobic domains that can insert into membranes at low pH and appear to be important for diphtheria toxin entry.

Antibodies directed against cell surface antigens have been linked to intact diphtheria toxin or its A subunit to selectively kill antigen-bearing target cells. Antibody-toxin (immunotoxins) or ligand toxin conjugates containing only the diphtheria A-chain have relatively low cytotoxic activity. Intact diphtheria toxin conjugates can be very potent, but can also have greater toxicity to normal cells. Since the B-chain appears to facilitate entry of the A-chain to the cytosol, it is possible that its presence in whole toxin conjugates renders them more potent, although less specific. Efforts have been made to construct more potent and specific immunotoxins by separating the toxin B-chain domains involved in cell binding from the domains involved in A-chain entry.

Target cell toxicity of immunotoxins can be increased by including the toxin B-chain in the antibody-toxin complex or by adding it separately. To achieve maximal in vitro target-cell selectivity with immunotoxins containing intact ricin, lactose must be added to the medium to block non-target-cell binding and toxicity of the immunotoxin via the ricin B-chain. This approach is feasible in those clinical settings, such as bone marrow transplantation, where the target cell population can be incubated in vitro in the presence of lactose. Without blockage of the B-chain binding domain, however, whole toxin conjugates have a high degree of non-target-cell toxicity, thereby limiting their usefulness in vivo.

Construction of reagents that combine the potency of intact toxin conjugates with the cell-type selectivity of toxin A-chain conjugates may be possible if the binding site on the toxin B-chain could be irreversibly blocked. Covalent and noncovalent chemical modifications that block the binding activity of ricin intracellularly also block its entry function, suggesting that the binding and translocation functions may be inseparable.

Previously, domain deletion was unsuccessfully used in an attempt to separate the translocation and the binding functions of diphtheria toxin B-chain. Immunotoxins made with the A-chain, intact diphtheria toxin, and a cloned fragment of diphtheria toxin (MspSA) that lacks the C-terminal 17-kDa region of the B subunit were compared. The intact diphtheria conjugate was 100 times more toxic than the MspSA conjugate was, which, in turn, was 100-fold more toxic than was the diphtheria toxin A-chain conjugate. The C- terminal, 17-kDa region, which contains the cell surface binding site, therefore potentiates immunotoxin activity 100-fold. It has not been possible to determine whether this C-terminal translocation activity was distinct from the binding activity.

Laird and Groman, *J. Virol.* 19: 220 (1976) mutagenized Corynebacterium with nitrosoguanidine and ultraviolet radiation and isolated several classes of mutants within the diphtheria toxin structural gene. Leppla and Laird further characterized several of the mutant proteins and found that three of them, CRM 102, CRM 103, and CRM 107, retained full enzymatic activity but had defective receptor binding.

Recombinant DNA technology has been used to improve immunotoxin efficacy at the gene level. Greenfield et al. (1984) in *Proc. Natl. Acad. Sci. USA* 80: 6953–6857, reported that they have cloned portions of diphtheria toxin and created a modified toxin which contains the N-terminal hydrophobic region of diphtheria toxin but lacks the C-terminal cysteine for ease of linking to antibodies. This fragment lacks the cell surface-binding sits of diphtheria toxin but includes most of the hydrophobic region thought to facilitate membrane transport.

Although cleavage of ricin or diphtheria toxin into A and B-chains had been thought to improve the specificity of the immunotoxins produced from the A-chain, cleavage of ricin or diphtheria toxins into A and B-chains removes the portion of the molecule containing residues important for transport into the cytosol of the cell. Specific cytotoxic reagents made by coupling toxin A subunits to antibodies have low systemic toxicity but also very low tumor toxicity. More potent reagents can be made by coupling intact toxins to monoclonal antibodies, as detailed in *J. Immunol.* 136: 93–98 and *Proc. Natl. Acad. Sci. USA* 77:5483–5486. These reagents, however, have a high systemic toxicity due to the toxin binding to normal cells, although they can have applications in vitro in bone marrow transplantation (cf. *Science* 222: 512–515).

It was found by Youle et al., as reported in *Jour. Immunol.*, op. cit., that monoclonal antibody-intact diphtheria toxin conjugates reacted quite differently from the intact ricin immunotoxins. Of the four reagents examined, a monoclonal antibody against type T3 antigen linked to diphtheria toxin (UCHT1-DT) had unique properties. This reagent showed greater selectivity in its toxicity to T cells as compared to stem cells than UCHT1-ricin. UCHT1-DT was found to be 10 to 100 times more selective than any previously reported immunotoxin.

Neville et al., in U.S. Pat. Nos. 4,359,457 and 4,440,747, disclose that the receptor specificity of toxins can be altered by coupling the intact toxin to monoclonal antibodies directed to the cell surface antigen Thy 1.2. However, the only toxin specifically disclosed to be treated in this manner is ricin. The same inventors in U.S. Pat. No. 4,500,637, disclose the covalent linkage of a monoclonal antibody known as TA-1 directed against human T-cells for use in treating human donor bone marrow before the marrow is fused into a human recipient. Thus, this reagent has been found to be useful in preventing graft versus host disease.

Another method of treating ricin to increase the rate of protein synthesis inhibition is by adding excess ricin B-chain to target cells independent of the amount of ricin A-chain bound to the cell surface membrane. The ricin A-chains used in this procedure are conjugated to anti-Thy 1.1 monoclonal antibodies. This process is disclosed in Neville et al., U.S. Pat. No. 4,520,011.

Yet another method of treating graft versus host disease is disclosed in Neville et al., U.S. Pat. No. 4,520,226. In this method, monoclonal antibodies specific for T-lymphocytes in human donor bone marrow are covalently linked to separate ricin toxin, combined in a mixture to form a treatment reagent, and combined with bone marrow removed from a human donor. The bone marrow-reagent mixture is then infused into an irradiated recipient, which virtually eliminates T-lymphocyte activity.

However, none of the prior art has shown effective immunotoxins prepared from diphtheria toxin which have the desired specificity and activity.

SUMMARY OF THE INVENTION

The present invention provides an improved anti-cancer therapy which is particularly efficacious against several malignancies including leptomeningeal carcinomatosis, leptomeningeal leukemia, and CSF-borne tumors. The compositions and methods taught herein provide means of treating both primary and metastatic lesions of the central nervous system.

The diphtheria conjugate using cell recognition moieties such as transferrin or anti-transferrin receptor monoclonal antibodies provide uniquely useful agents. The use of binding or cell recognition moieties consisting of monoclonal antibodies against the human transferrin receptor linked to a mutant form of diphtherial toxin, CRM 107, in which the binding function of the toxin has been inactivated by a point mutation at position 525 of the toxin B chain is a preferred embodiment taught herein.

DETAILED DESCRIPTION OF THE DRAWINGS

Figure 1A:
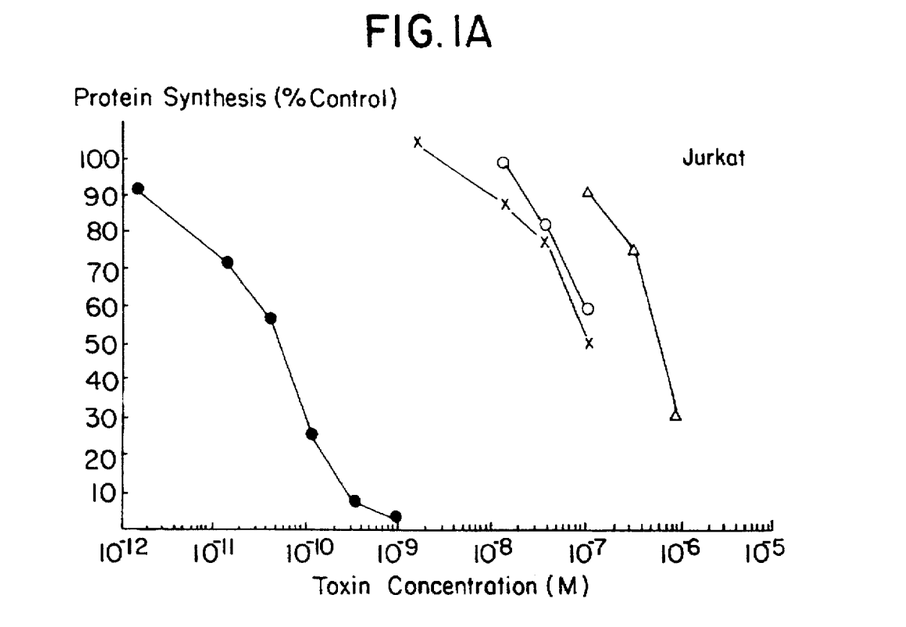
FIG. 1A shows a comparision of the toxicity of diphtheria toxin, CRM102, CRM103, and CRM 107 on Jurkat cells as compared to native diphtherial toxin using a sixteen hour protein synthesis assay.
Figure 1B:
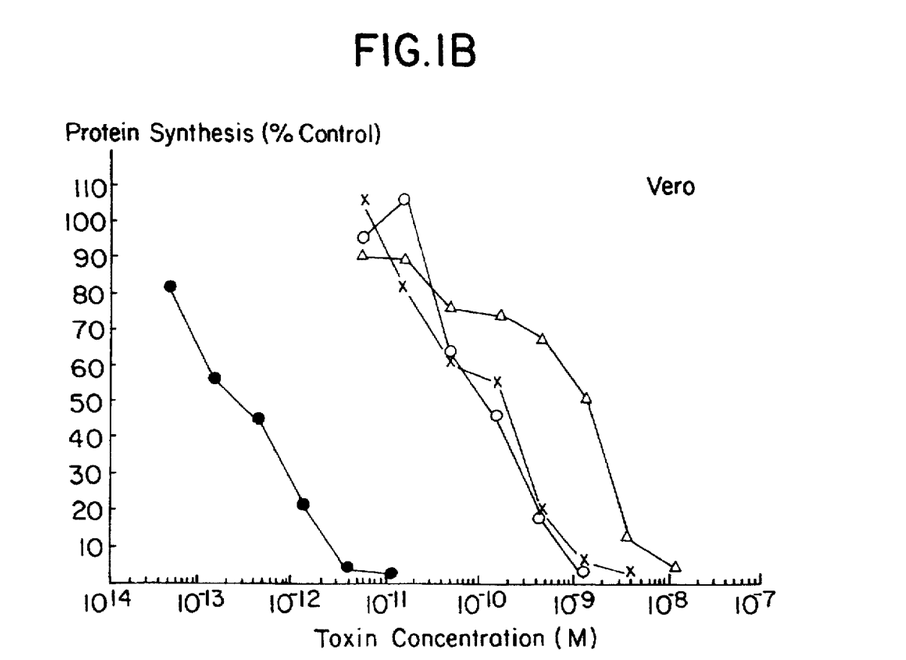
FIG. 1B shows toxicity for the diptheria toxins as in FIG. 1A, but upon Vero cells.

In FIG. 1, protein synthesis was assayed by incubating $5\times10^4$ Jurkat cells in 100 microliters leucine-free RPMI 1640 medium containing 2% FCS in 96-well microtiter plates. DT (●), CRM102 (X), CRM103 (○), or CRM107 (△) were added in 11 microliters buffer and incubated with cells for 16 hours at 37° C. Cells were then pulsed with 20 microliters of phosphate buffered saline containing 0.1 microCi of $^{14}$C-leucine, incubated for one hour at 37° C., harvested onto glass fiber filters by means of a PHD cell harvester, washed with water, dried, and counted. The results are expressed as a percentage of the $^{14}$C-leucine incorporation in mock-treated control cultures.

Figure 2:
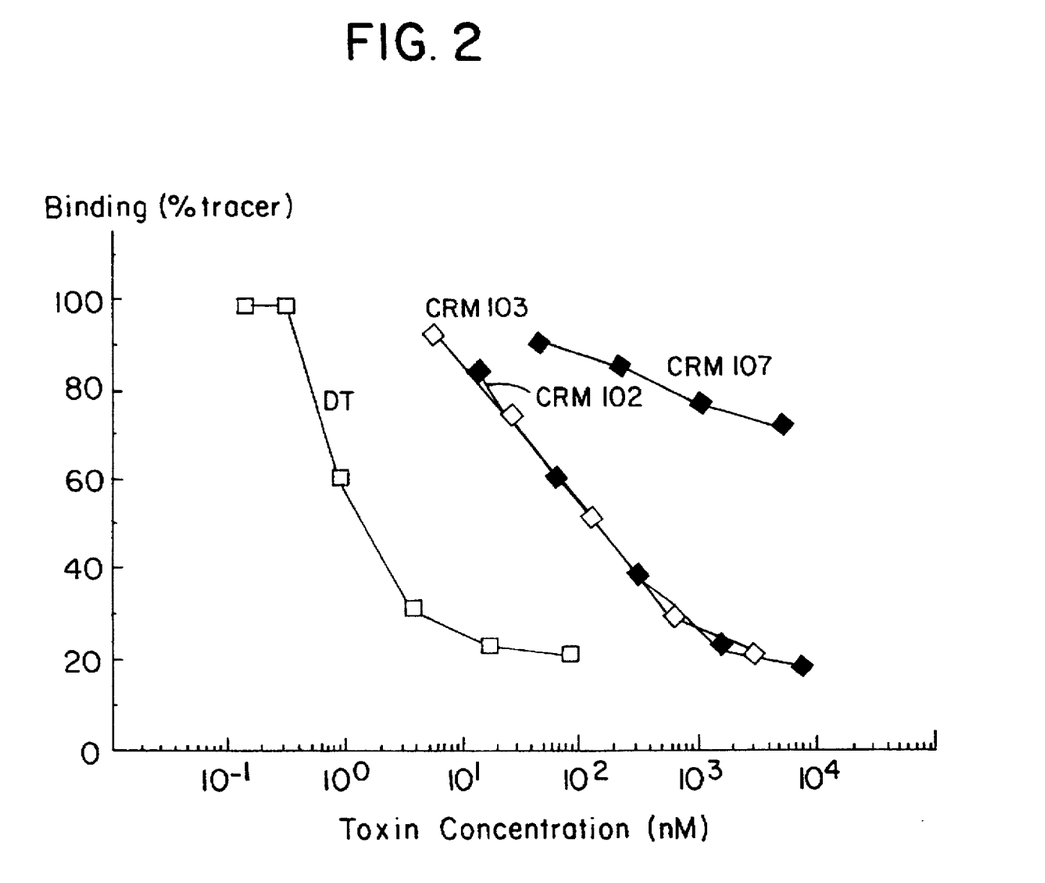
FIG. 2 shows the binding activity of native diphtheria toxin and the three CRM mutants to Vero cells.

In FIG. 2, tracer $^{125}$I-labelled DT binding was competed with cold DT (○), CRM102 (x), CRM103 (○), and CRM107 (△). DT was labelled with Biobeads to $7\times10^6$ cpm/microgram. Vero cells, plated that previous day at $5\times10^5$ cells/ml well in Costar 24-well plates, were incubated in 150 microliters DMEM and 10% FCS and 25 mM HEPES, pH 7.0, with 8 ng/ml $^{125}$I-labelled DT and appropriate concentrations of DT and CRMs. After incubating 6.5 hours at 4° C., the cells were washed four times in complete medium, solubilized in 0.1N NaOH, and counted. Tracer binding varied between 900 and 1500 cpm, depending upon the experiment. No nonspecific binding was subtracted.

Figure 3:
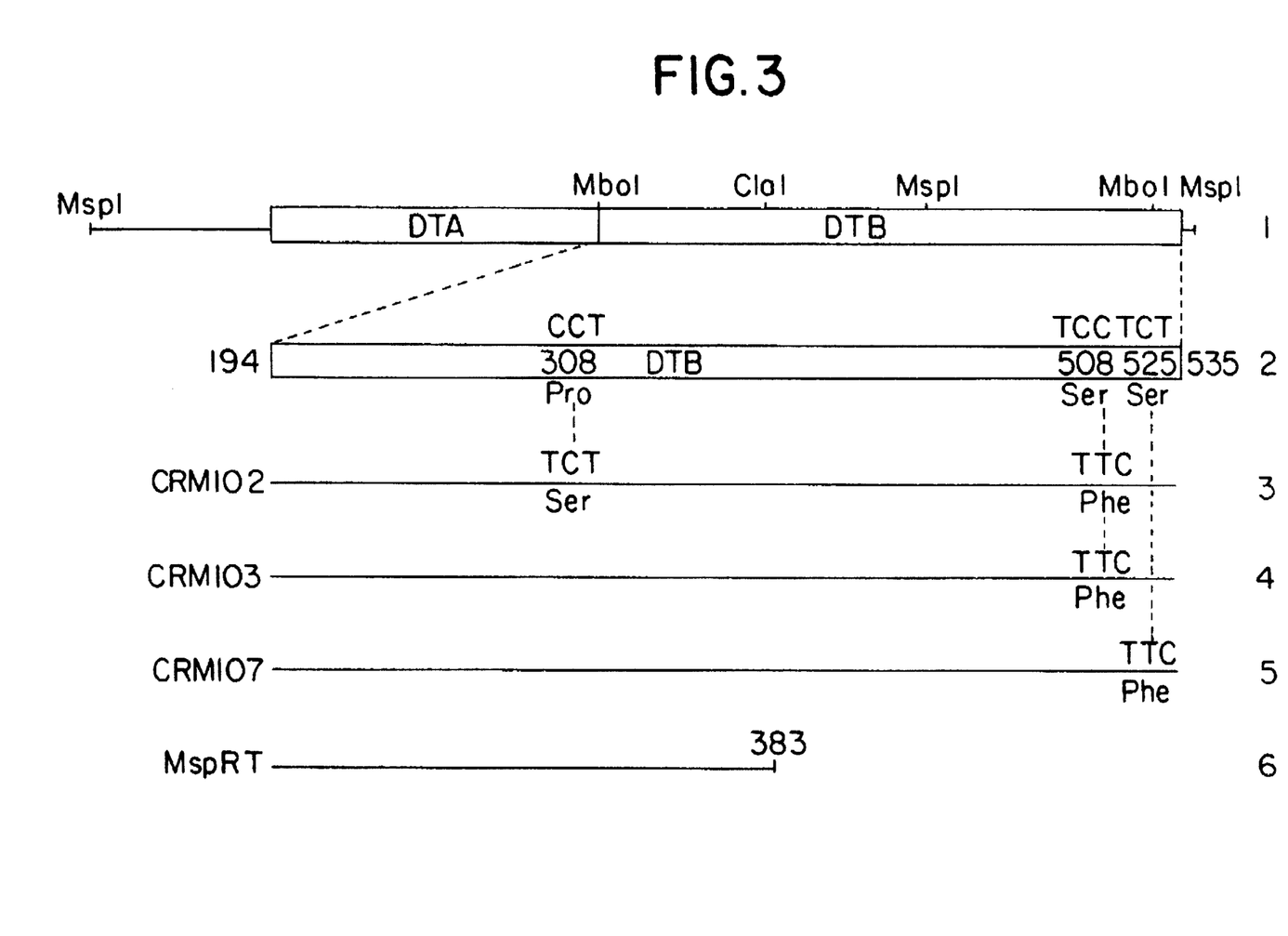
FIG. 3 shows the location of the CRM point mutations within the diphtheria structural gene.

In FIG. 3, line 1 shows the restriction map of the DT structural gene, indicating the location of the sites used for sequencing. Line 2 shows expansion of the B-chain structural region, indicating the native amino acid and DNA sequencing corresponding to the point mutations found within the CRMs. Mutations found within the B chain of CRM102, line 3, CRM103, line 4, and CRM107 line 5, are shown. Line 6 shows the end of the MspSA clone previously described. The sequences were obtained by cloning the two MboI-ClaI fragments into M13MP and M18MP19 and sequencing by the method of Sanger or by cloning the two MspI fragments into pBR-322 and sequencing by the method of Gilbert and Maxam.

Figure 4:
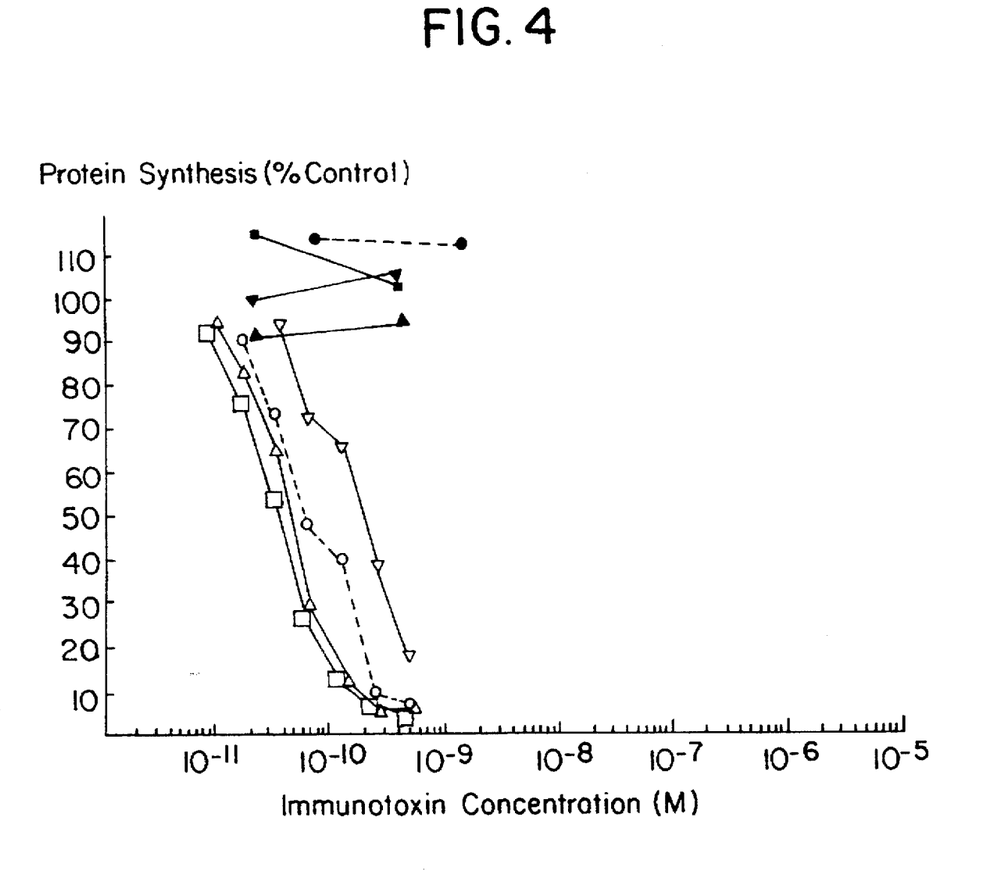
FIG. 4 shows a comparison of the toxicities of immunotoxins made by conjugating UCHT1 with CRM102, CRM103, and native diphtheria toxin.

In FIG. 4, the antibody was linked to the toxins via a thioether bond as described below. Immunotoxins were separated from unconjugated Ab and toxin by gel filtration on a TSK-3000 HPLC column. The immunotoxin peak was collected, and toxicity was evaluated with the protein synthesis assay described in the legend to FIG. 1. UCHTI-DT (○), UCHTI-CRM102 (∇), UCHTI, CRM103, (△), and UCHTI-CRM106 (□), were incubated with $5\times10^4$ Jurkat cells for sixteen hours, followed by a one hour pulse with $^{12}$C-leucine. Incubation with excess free UCHTI (100 micrograms/ml) blocked toxicity (closed symbols).

Figure 5:
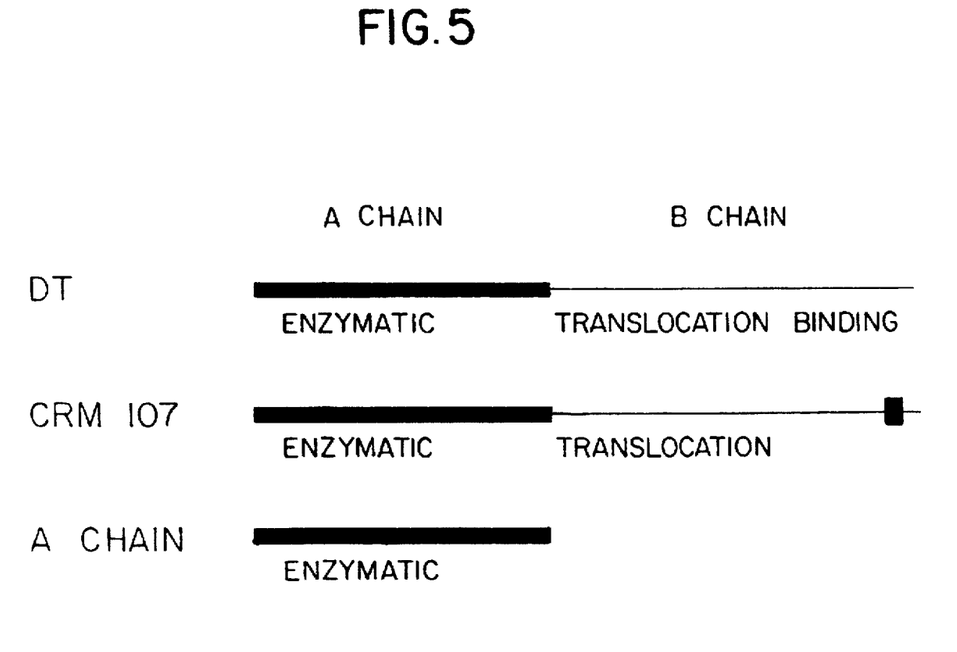
FIG. 5 is a diagrammatic representation of DT, CRM107, and DT A chain structure and function.

In the diagram shown in FIG. 5, native DT is composed of an A and B subunit with the A chain containing the enzymatic function and the B chain containing the binding and translocation function. Two point mutations in CRM107 inactivate the toxin binding function but leave the translocation and enzymatic function intact. Toxin A chain contains only the enzymatic function.

Figure 6A:
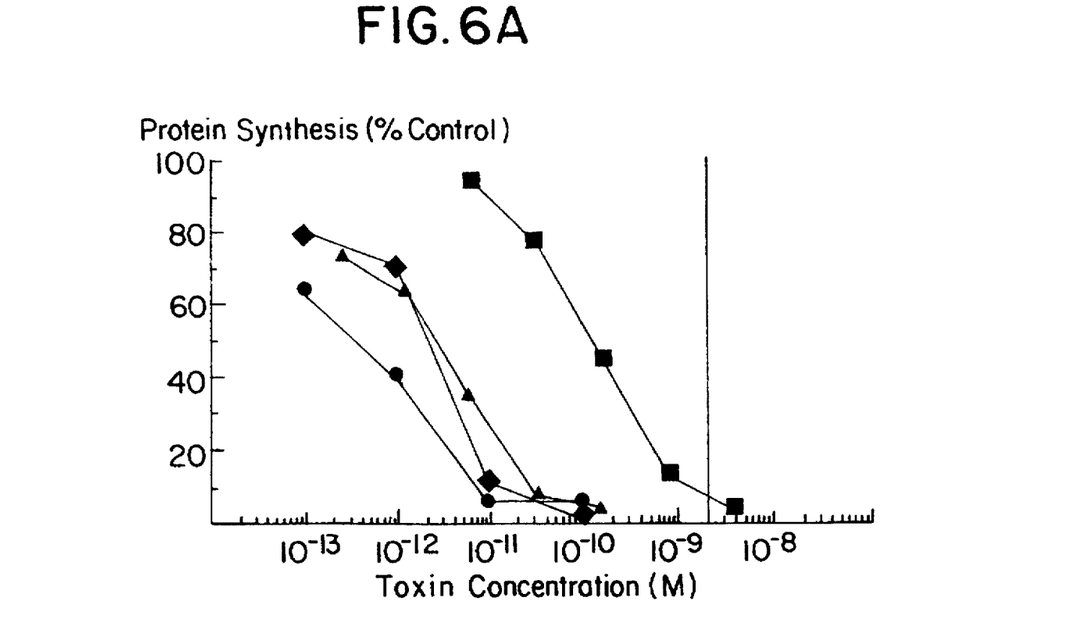
FIGS. 6A–B shows the cytotoxic effects of Tf-CRM107 on cells derived from medulloblastoma (A) and glioblastoma (B) compared to maximum tolerable levels achieved in the CSF of rhesus monkeys.
Figure 6B:
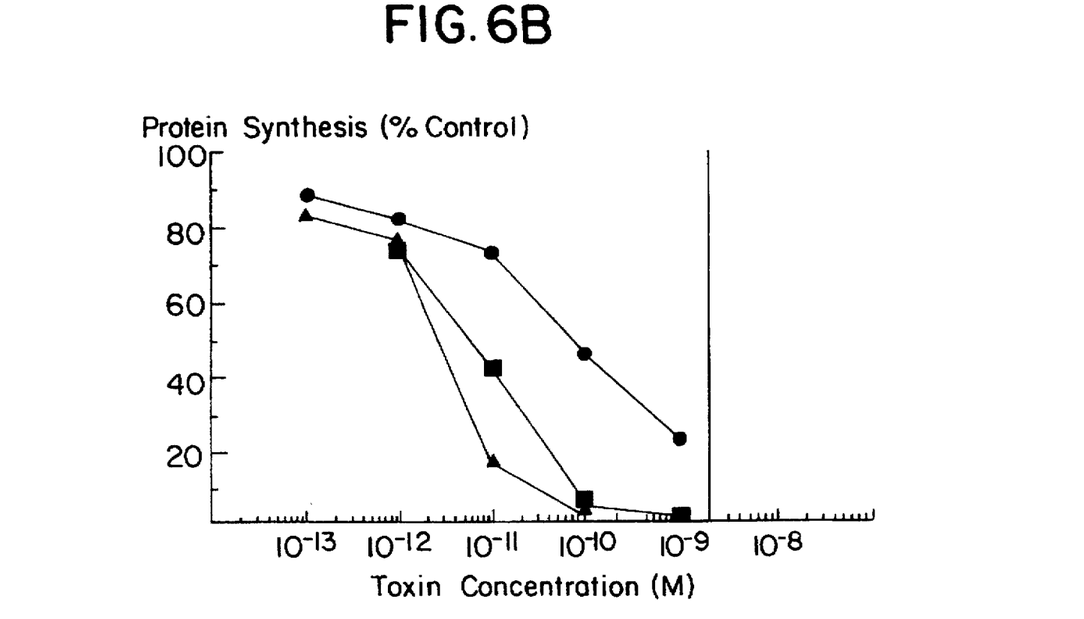

In FIG. 6, primary cultures or established cell lines were incubated for 24 hours with varying concentrations of Tf-CRM107 followed by one hour incubation with 0.1 microCi 14C-leucine. Cells from triplicate cultures were then harvested and protein synthesis in treated cells was expressed as a percentage of $^{14}$C-leucine incorporated into untreated control cells. Concentrations of $2\times10^{-9}$M of Tf-CRM107, injected intrathecally into the cisterna magna of Rhesus monkeys, could be reached safely (vertical line). FIG. 6A shows the dose response curves for medulloblastoma-derived cells, SNB105; SNB104; TE671; SNB40. FIG. 6B shows the dose response curves for glioblastoma-derived cells: SNB75; U251; SNB101.

Figure 7:
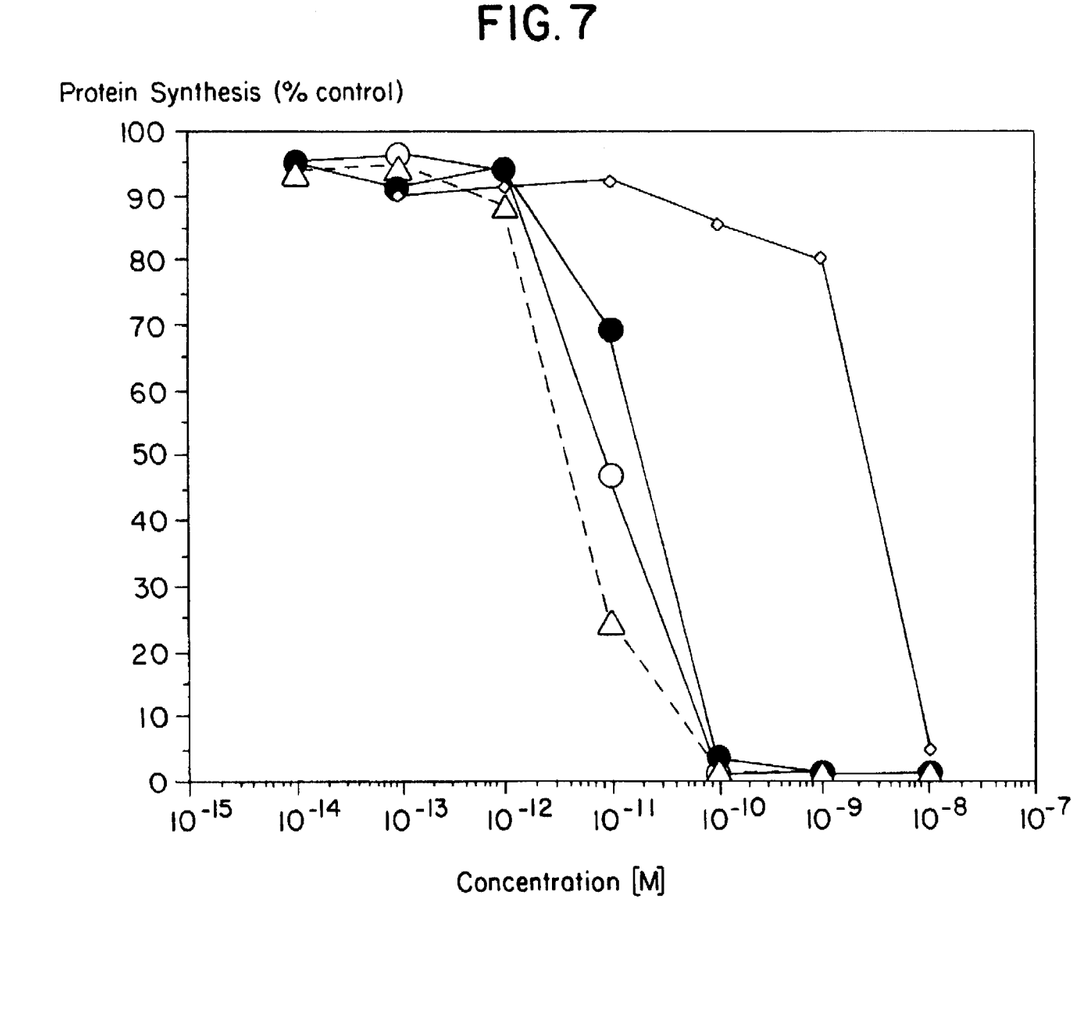
FIG. 7 shows a comparison of the toxicity of three anti-transferrin receptor monoclonal antibodies linked to CRM107.

FIG. 7 shows a comparison of the toxicity of three monoclonal antibodies against the human transferrin receptor. T56/14 (○), B3/25 (●), and 454A12 (△) were all linked to CRM 107 and their toxicities compared using K562 cells. Unconjugated native diphtheria toxin (□) was also tested.

Figure 8A:
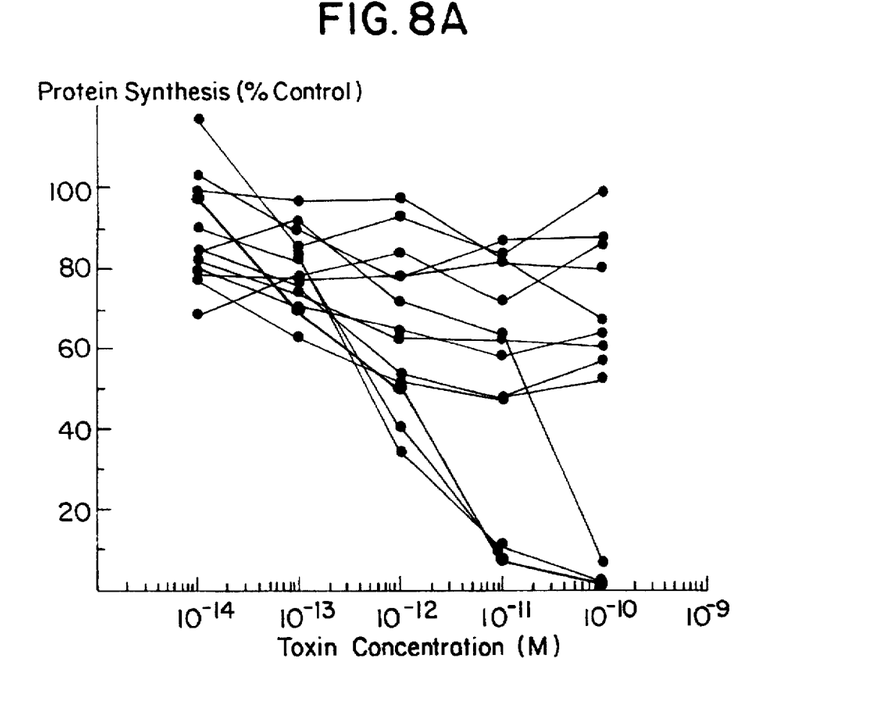
FIGS. 8A–B shows the inhibition of DT cytotoxicity by human serum or CSF.
Figure 8B:
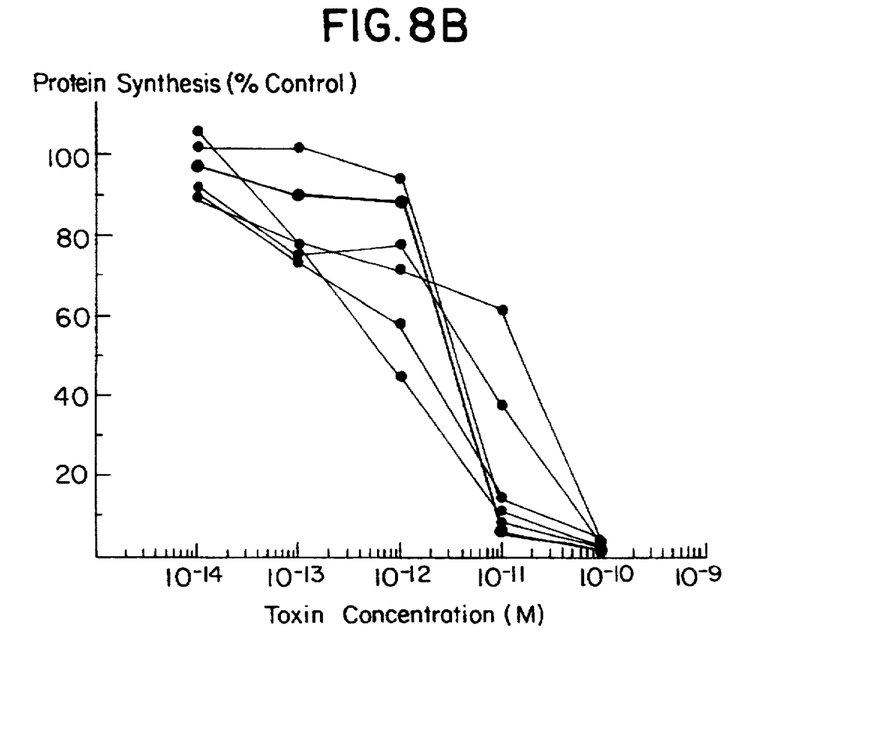

In FIG. 8, Vero cells, derived from green monkey kidney, have high levels of DT receptors (1.6×105 sites per cell) and as a result are extremely sensitive to DT toxicity. Vero cells were therefore used to determine the presence of anti-DT antibodies in the serum and CSF of normal volunteers. Dilutions of DT were preincubated with an equal volume of undiluted serum or CSF for thirty minutes at room temperature. Twenty-two microliters of the preincubated DT mixtures were added to the Vero cells and incubated for fourteen hours. Cytotoxicity assays were performed and the results were expressed as described in the Detailed Description of the Invention. DT control, preincubated with PBS rather than serum or CSF, is plotted as a bold line. The effect of preincubation of DT with serum, FIG. 8A or CSF, FIG. 8B from normal volunteers is shown by thin lines.

DETAILED DESCRIPTION OF THE INVENTION

The present invention provides mutants of diphtheria toxin which are conjugated to a binding moiety which is a binding agent which binds specifically to a cell, cell type, or specific receptor. The binding agent may be a monoclonal antibody, transferrin, or epidermal growth factor, for which receptors are found in a great variety of human tumor cells. The conjugates of the present invention can be used to prepare formulations for treating a great variety of tumors without the undesirable effects of native diphtheria toxins on the patients.

More particularly, immunotoxin conjugates are provided consisting of diphtheria toxin or a like toxin having one or two point mutations, coupled to either anti-transferrin monoclonal antibodies or transferrin. This conjugate is particularly toxic towards human primary brain tumors, metastatic tumors to the brain, CSF-born tumors, leptomeningeal leukemia, and leptomeningeal carcinomatosis.

Immunotoxins were made by conjugating three forms of diphtheria toxin, CRM102, CRM103, and CRM107. (cf. *J. Virology* 19:220–227, 1976) that differ in only one or two amino acids from native diphtheria toxin in the C region with UCHT1, a monoclonal antibody to the T3 antigen receptor found on human T-cells, or to transferrin, or to any one of a number of known binding agents such as epidermal growth factor or polyclonal sera of certain types. The conjugation used a slight modification of previously published procedures (PNAS 77:5483–5486, 1980).

The phenotypic designation CRM is used to designate the protein product of a tox gene that is serologically identical with diphtheria toxin.

The nontoxinogenic mutants of corynebacteriophage beta have been classified into four major classes. Class I consists of ten mutants, each of which produces a protein that forms a line of identity with diphtheria toxin when tested by immunodiffusion against diphtheria antitoxin. These mutants probably represent missense mutations in the structural gene for toxin. The mutants in subclass 1A give a positive skin test but a negative tissue culture test. Two possible explanations are that the mutant protein has a low level of activity or is produced in smaller amounts.

Class II mutants produce proteins that form lines of partial identity with toxin when tested against antitoxin by immunodiffusion. On slab gel electrophoresis, only one of these proteins was detected, but, based on immunodiffusion tests, all appear to be smaller than purified toxin. Either a deletion, a nonsense mutation in the structural gene for toxin, or preferential proteolysis could account for the shortened polypeptide.

Class III mutants produce two proteins serologically related to toxin, two lines being detected in the immunodiffusion test. One line shows full identity with purified toxin, and the other shows only partial identity.

Class IV mutants do not produce a protein serologically related to toxin, nor are they capable of eliciting a positive guinea pig skin test. The phenotype of these mutants has been designated CRM-. This would indicate that the intact toxin molecule is either not produced or is produced or excreted in very small amounts. This CRM-phenotype couple results from such mutational events as a deletion, a very early nonsense mutation in the toxin structural gene leading to the production of small fragments of toxin, or a mutation in a regulatory site or gene.

The CRM102, CRM103, AND CRM 107 have not been classified in one of the four major classes of mutants of diphtheria toxin, although immunodiffusion shows complete antigenic homology with diphtheria toxin. The molecular weight of these three CRM's was determined by electrophesis to be in the range of about 62,000.

Diphtheria toxin and CRM102, CRM103, and CRM107 were conjugated to m-maleimidobenzoyl N-hydroxysuccinimide ester (MBS) by incubating the toxins with a 10-fold excess of MBS for thirty minutes at room temperature. The mixture was then applied to a G-25 column to remove free MBS from the toxin. UCHT1 was reduced with 10 mM dithiothreitol for 30 minutes at room temperature, and free DTT was separated from the antibody on a G-25 column. MBS-conjugated toxin was mixed with reduced antibody and incubated at room temperature for three hours. Immunotoxins were separated from unconjugated antibody and toxin by gel filtration on a TSK-3000 HPLC column.

Peak fractions containing the immunotoxins were collected and tested for toxicity to an antigen positive human leukemic T-cell line. Protein synthesis was assayed by incubating $10^5$ cells in 100 microliters of leucine-free RPMI 1640 containing 2% fetal calf serum in 96 well microtiter dishes. Toxins, immunotoxins, and control buffers (11 microliters) were incubated with the cells for sixteen hours at 37° C. Twenty microliters of phosphate buffered saline containing 0.1 microCurie of $^{14}$C-leucine was then added for 60 minutes. Cells were harvested onto glass fiber filters using a PHD cell harvester, washed with water, dried, and counted. The results are expressed as percentage of $^{14}$C incorporation in mock-treated control cultures.

FIG. 1 shows the toxicity of CRM102, CRM103, CRM104, and native diphtheria toxin to Jurkat cells (A) and Vero cells (B). Protein synthesis was assayed by incubating $5\times10^4$ Jurkat cells in 100 microliters leucine-free RPMI 1640 medium containing 2% FCS in 96-well microtiter plates.

DT (●), CRM102 (X), CRM103 (○), or CRM107 (Δ) were added in 11 microliters buffer and incubated with cells for 16 hours at 37° C. The cells were then pulsed with 20 microliters of PBS containing 0.1 microCurie of $^{14}$C-leucine, incubated for one hour at 37° C., harvested onto glass fiber filters by means of a PHD cell harvester, washed with water, dried, and counted. The results are expressed as a percentage of the $^{14}$C-leucine incorporation in mock-treated control cultures.

Vero cells have a higher number of diphtheria toxin receptors than do Jurkat cells, and are thus more sensitive to diphtheria toxin inhibition of protein synthesis than are Jurkat cells. CRM102 and CRM103 are 1000-fold less toxic than native diphtheria toxin is, and CRM107 is 10,000-fold less toxic than native diphtheria toxin is to both Vero cells and Jurkat cells.

FIG. 2 shows the binding activity of native diphtheria toxin and the three CRM mutants to Vero cells. While most cell types, including lymphoid cells such as Jurkat, have undetectable levels of diphtheria toxin receptors, Vero cells contain $10^5$ diphtheria toxin receptors per cell and have been used extensively to study diphtheria toxin binding. At 4° C.

the affinity of both CRM102 and CRM103 is 100-fold less than that of native diphtheria toxin, and the affinity of CRM107 is 8000-fold less than that of native diphtheria toxin.

The reduced affinity correlates with the reduced toxicity for CRM107 but differs by 10-fold for CRM102 and CRM103. Binding was determined after six hours at 4° C., while toxicity was determined after 24 hours at 37° C. The discrepancy between binding and toxicity for CRM102 and CRM103 may reflect differences in temperature and time in the two assays. Binding cannot be determined at 37° C. since energy inhibitors commonly used to block internalization decrease the number of surface diphtheria toxin receptors. Alternatively, the mutations within CRM102 and CRM103 may inhibit toxin activities other than binding that may account for the 10-fold difference between toxicity and binding.

FIG. 3 shows the location of the amino acid changes within the B-chain for each of the three mutations. CRM103 contains a single mutation at position 508 (Ser-PHE). CRM102 contains a similar mutation at position 508, but has an additional mutation at position 308 (Pro-Ser). CRM107 contains a single mutation at position 525 (Ser-Phe). That CRM102 has two mutations while CRM103 contains only one indicates that the two mutants are independent isolates. The presence of multiple GC-AT transitions is consistent with nitrosoguanidine-induced mutagenesis. The truncated clone shown as the last line represents the MspSA clone described above.

Line 1 is the restriction map of the diphtheria toxin structural gene, indicating the location of the sites used for sequencing. Line 2 is the expansion of the B-chain structural region, indicating the native amino acid and DNA sequence corresponding to the point mutations found within the CRM's. Mutations found within the B-chain of CRM102 (line 3), CRM103 (Line 4), and CRM107 (line 5) are shown. Line 6 shows the end of the MspSA clone previously described. The sequences were obtained by cloning the two MboI-ClaI fragments into M13MP and M13MP19 and sequencing by the method of Sanger et al., J. Mol. Biol. 162, 729 (1982), or by cloning the two MspI fragments into pBR322 and sequencing by the method of Gilbert and Maxam, Methods Enzymol. 65, 499 (1980).

The 100-fold decreased binding affinity of CRM103 and CRM102 demonstrates that the serine at position 508 is important for toxin binding. The single mutation in CRM107 suggests that the alteration at position 525 causes the 8000-fold decrease in binding activity. The mutations at positions 508 and 525 are consistent with data which suggest that the diphtheria toxin binding domain lies within the carboxyl 17-kDa portion of the molecule. Both mutations exchange a phenylalanine for a serine.

The relationship of binding to translocation in diphtheria toxin was examined by linking each of the CRM's and native diphtheria toxin to a new binding domain, the monoclonal antibody UCHT1, which is specific for the T3 antigen on human T-cells.

FIG. 4 shows that, unlike the unconjugated CRM's, all three CRM immunotoxins are highly toxic. Excess antibody blocks toxicity, demonstrating that the toxicity is antibody-mediated. The immunotoxins prepared with CRM103 and CRM107 are equally toxic as the immunotoxin prepared with native diphtheria toxin, whereas the immunotoxin prepared from CRM102 is approximately 10-fold less toxic. The 10-fold decrease in UCHT1-CRM102 toxicity relative to UCHT1-CRM103, despite identical binding activity of CRM102 and CRM103, suggests that the amino acid at position 308 contributes to the translocation activity of diphtheria toxin. That the conjugates prepared with CRM103 and CRM107 are as toxic as are conjugates prepared with native diphtheria toxin indicates that binding of the toxin to its receptor is not necessary for efficient translocation of the toxin-A fragment to the cytosol. Therefore, the diphtheria toxin binding and translocation functions can be separated.

FIG. 4 shows the comparison of the toxicities of immunotoxins made by conjugating UCHT1 with CRM102, CRM103, CRM107, and native diphtheria toxin. The antibody was linked to the toxins via a thioether bond as described previously. Immunotoxins were separated from unconjugated antibody and toxin by gel filtration on a TSK-3000 HPLC column. The immunotoxin peak was collected, and toxicity was evaluated with the protein synthesis assay as described in FIG. 1. CHT1-DT (O), UCHT1-CRM102 ($\triangledown$), UCHT1-CRM103 ($\triangle$), and UCHT1-CRM107 ($\square$) were incubated with $5 \times 10^4$ Jurkat cells for sixteen hours, followed by a one hour pulse with $^{14}$C-leucine. Incubation with excess free UCHT1 (100 micrograms/ml) blocked toxicity.

As shown in both FIGS. 1 and 4, native diphtheria toxin and UCHT1-diphtheria toxin inhibit Jurkat cell protein synthesis 50% at $3\times10^{-11}$M. The selective toxicity of UCHT1-DT to T3 bearing cells is 100-fold, and exists solely because crosslinking diphtheria toxin to antibody inhibits diphtheria toxicity 100-fold. The mutant toxins, CRM102, CRM103, and CRM107, inhibit Jurkat cell protein synthesis 50% at $1\times10^{-7}$M to $4\times10^{-6}$M (FIG. 1), whereas the UCHT1-CRM immunotoxins act at $3\times10^{-11}$M to $3\times10^{-10}$M (FIG. 4). This 1000–10,000-fold difference in concentration between the CRM's and the UCHT1-CRM's required to inhibit protein synthesis represents a three to four order of magnitude increase in CRM immunotoxin selectivity over the native diphtheria immunotoxin.

The toxicities of the different immunotoxins were compared on non-target Vero cells, which lack antibody-binding sites but express a high number of diphtheria toxin cell-surface binding sites. UCHT1-DT inhibits Vero protein synthesis 90% at $6\times10^{-10}$M, because of toxicity via the diphtheria toxin binding site. In contrast, all three CRM immunotoxins had no effect on protein synthesis at this concentration. Thus, the loss of toxicity of the CRM's, as shown in FIG. 1, is exhibited also by the CRM immunotoxins on non-target cells.

The immunotoxins as described herein can also be conjugated with human transferrin (Tfn). Transferrin is highly conserved across species and, as a result, human transferrin exhibits species cross-reactivity that enables the comparison of the toxicity of transferrin-toxin conjugates on cells derived from human (Jurkat, K562), monkey (Vero), and mouse (Wehi, EL-4), as shown in Table 1.

TABLE I

$IC_{50}$ of DT and Tfn-Toxin Conjugates on Various Cell Lines

| Cell Line | Source | DT | Tfn-DT | Tfn-CRM107 | CRM107 |
|---|---|---|---|---|---|
| Vero | Monkey kidney | $8 \times 10^{-13}M^{(a)}$ | $1.9 \times 10^{-11}M$ | $1.4 \times 10^{-10}M$ | $8 \times 10^{-9}M$ |
| K562 | Human Erythroleukemia | $3.4 \times 10^{-10}M$ | $9 \times 10^{-13}M$ | $1.6 \times 10^{-12}M$ | $3.4 \times 10^{-6}M^{(c)}$ |
| Jurkat$^{(b)}$ | Human T-cell leukemia | $6.1 \times 10^{-11}M$ | $4 \times 10^{-12}M$ | $2 \times 10^{-12}M$ | $5.4 \times 10^{-7}M$ |
| El-4 | Mouse T-cell lymphoma | $2.8 \times 10^{-7}M$ | $1.6 \times 10^{-11}M$ | $8 \times 10^{-12}M$ | $2.8 \times 10^{-3}M^{(c)}$ |
| Wehl | Mouse T-cell lymphoma | $2.4 \times 10^{-7}M$ | $4.8 \times 10^{-12}M$ | $8.5 \times 10^{-12}M$ | $2.4 \times 10^{-3}M^{(c)}$ |
| MCF7 | Human breast adenocarcinoma | $1.1 \times 10^{-11}M$ | $2.8 \times 10^{-11}M$ | $1 \times 10^{-10}M$ | |
| TE61 | Human medulloblastoma | $3.7 \times 10^{-11}M$ | | $3.5 \times 10^{-12}M$ | |
| SNB 40 | Human medulloblastoma | $1.7 \times 10^{-11}M$ | | $1.4 \times 10^{-11}M$ | |
| SNB 75 | Human glioblastoma | $4.6 \times 10^{-13}M$ | | $5.0 \times 10^{-12}M$ | |

$^{(a)}$Concentrations shown are the concentrations that inhibit protein synthesis by 50% of control values.
$^{(b)}$Jurkat cells were incubated with toxins for 16 hrs. followed by a 1 hr pulse with $^{14}$C-Leu. All other cell lines were incubated for 24 hrs followed by a 1 hr pulse.
$^{(c)}$These concentrations are assumed, based on the 10,000-fold reduction in CRM107 toxicity observed in both Vero and Jurkat cells. Limitations imposed by the concentration of CRM107 did not permit direct measurements.

Before conjugating the toxin with transferrin, human transferrin (Tfn) was loaded with iron according to the method of Shindelman et al., (1981), *Int. J. Cancer* 27:329. The conjugation of Tfn was accomplished by first generating free sulfhydryl groups on Tfn with 2-iminothiolane. The 2-iminothiolane was dissolved in 0.8M boric acid, pH 8.5, and incubated with Tfn in an 8:1 molar ration. After a one hour incubation at room temperature, the modified Tfn was separated from the 2-iminothiolane by gel filtration on a G-25 column. M-maleimidobenzoyl N-hydroxysuccinimide (MBS) was dissolved in dimethylformamide and added in five-fold molar excess to the toxin, which was either native diphtheria toxin, CRM102, CRM103, or CRM107. This mixture was incubated for thirty minutes at room temperature, and free MBS was removed from the toxin by chromatographic separation using a G-25 column. The MBS-conjugated toxin was mixed with thiolated transferring in 1:1.3 molar ration and incubated for three hours at room temperature. Immunotoxins were purified by gel filtration on a TSK-3000 HPLC column.

Species cross-reactivity enables one to evaluate the toxicity and the effectiveness of the toxin conjugate in animal models as well as to examine the effectiveness of the Tfn-toxin conjugate in a wide variety of human tumors. Tfn-CRM107, when assayed on Jurkat cells, exhibited a 400,000-fold differential in toxicity over CRM107 alone. This represents a considerable improvement in the 10,000-fold selectivity previously observed between UCHT1-CRM107 and CRM107 on Jurkat cells.

It has also been found that K562, a human erythroleukemia cell line characterized by high levels of transferrin receptors, is also sensitive to Tfn-CRM107. Assuming that the binding and toxicity of CRM107 is reduced by 10,000-fold relative to diphtheria toxin on K562 cells, as it is on Vero and Jurkat cells, then the differential in toxicity between CRM107 and Tfn-CRM107 for K562 cells is greater than one million. Binding of the toxin conjugates was Tfn-mediated as shown by the fact that free Tfn completely inhibits toxicity, as shown in Table 2.

TABLE 2

INHIBITION OF TOXICITY BY FREE UCHT1 OR TFN

| Toxin | Cell Line | Protein Synthesis % Control |
|---|---|---|
| UCHT1-CRM107 ($4 \times 10^{-10}M$) | Jurkat | 3.9 |
| UCHT1-CRM107 ($4 \times 10^{-10}M$) + free UCHT1 (100 µg/ml) | Jurkat | 94.5 |
| Tfn-CRM107 ($3.6 \times 10^{-10}M$) | K562 | 0.7 |
| Tfn-CRM107 ($3.6 \times 10^{-10}M$) + free Tfn (300 µg/ml) | K562 | 100.3 |
| Tfn-DT ($2.3 \times 10^{-10}M$) | K562 | 2.4 |
| Tfn-DT ($2.3 \times 10^{-10}M$) + free Tfn (300 µg/ml) | K562 | 110.3 |

Synthesis of CRM 107 Immunotoxins

CRM 107 was purified from culture supernatant by ammonium sulphate precipitation followed by anion exchange chromatography using DE-52. Purified CRM 107 was conjugated to the anti-transferrin monoclonal antibody using a thioether linkage. Conjugation of the monoclonal antibody with CRM 107 was accomplished by first generating free sulfhydryl groups on the antibody with 2-iminothiolane. This modified monoclonal antibody was then linked to the toxin using m-Maleimidobenzoyl-n-hydroxysuccinimide ester (MBS). Free MBS was removed by gel filtration on a Sephadex G-25 column and immunotoxin conjugates were separated from free antibody and free toxin by size exclusion on a TSK-3000 HPLC column.

Demonstration of in vitro Efficacy of Anti-Transferrin Monoclonal Antibodies Linked to CRM 107

A variety of different monoclonal antibodies against the human transferrin receptor were conjugated with CRM 107 and the in vitro efficacy compared (FIG. 7). All of the anti-transferrin receptor monoclonal antibodies tested (T56/14, B3/25, 454A12) were highly toxic to K562, an erythroblastoma cell line. $IC_{50}$ values ranged between $5 \times 10^{-12}$ and $2 \times 10^{-11}M$.

Similarly, a variety of cell lines have been tested to establish the in vitro efficacy of an immunotoxin composed of an anti-transferring receptor monoclonal antibody linked with CRM 107 for the treatment of leptomeningeal carcinomatosis, leptomeningeal leukemia, primary brain tumors, metastatic brain tumors and CSF-borne tumors. SNB 75 cell line was established by primary explants from a tumor removed from a 72 year old woman with a bifrontal glioblastoma multiforme. SNB 101 was also established by primary explants from a glioblastoma multiforme removed from right parietal lobe of a 49-year-old man. SNB 40 was derived from primary explants of a medulloblastoma surgically removed from the posterior fossa of an eight-year-old boy. U251 is a cell line of human glioma origin adapted to culture by J. Ponten and B. Westermark at the University of Uppsala, Uppsala, Sweden.

Since established cell lines long adapted to culture conditions could conceivably possess transferrin requirements and receptor levels different from those of the original cells, two primary medulloblastoma cultures were established. SNB 104 was established from a biopsy of a midline cerebellar vermian mass in an 18-year-old male. SNB 105 was derived from a midline posterior fossa tumor in a 5-year-old girl.

Two of the most common types of leptomeningeal carcinomatosis originate from primary tumors of the breast or lung. Therefore, three cell lines derived from human breast cancers and three cell lines derived from small cell carcinoma of the lung were examined. MCF7 is a cell line derived from a breast adenocarcinoma. ZR-75.1 was derived from a malignant ascitic effusion from a patient with infiltrating ductal carcinoma and T47D was derived from an infiltrating ductal carcinoma. The three cell lines derived from small cell carcinoma were 417, 510, and 209.

CRM 107-based immunotoxins inhibit protein syntheis which, in turn, can be measured for an accurate in vitro assessment of the lethal effect of the immunotoxin on cells. The efficacy of an immunotoxin composed of a monoclonal antibody against the human transferrin receptor (454A12, deposited at the American Type Culture Collection, 12301 Parklawn Drive, Rockville, Md., in connection with a patent application, but restricted at the time of filing of this application linked to CRM 107 (454A12-CRM 107) was compared with that of native transferrin linked to CRM 107 (Tfn-CRM 107). The monoclonal antibody binds to only human transferrin receptors and therefore prohibits accurate toxicity studies in animals. However, transferrin is able to cross species boundaries thus allowing accurate toxicity trials in a variety of animal species to be carried out.

Table III lists the sensitivity of cell lines derived from small cell carcinomas to 454A12-CRM 107 immunotoxins. These $IC_{50}$ values are reflective of a short exposure (4 h) of the cells to the toxin yet even after this short exposure potent cell killing is apparent.

FIG. 6*a* illustrates representative dose-response curves of the Tfn-CRM 107 conjugate on four medulloblastoma-derived cell lines. A steep dose-response inhibition of protein synthesis by Tfn-CRM107 was observed with all the cell lines. A comparison between the $IC_{50}$ of Tfn-CRM 107 and 454A12-CRM 107 is shown in Table IV.

FIG. 6*b* shows results of similar experiments using the glioblastoma-derived cell lines. As observed with cells derived from medulloblastoma, Tfn-CRM 107 exhibited potent killing with all of the glioblastoma cells. Using a monoclonal antibody against the transferrin receptor, 454A12, linked to CRM 107 on the medulloblastoma and glioblastoma cell lines showed $IC_{50}$ levels between $10^{-11}$ and $10^{-10}$M, whereas, when this same conjugate was assayed on Vero cells, which lack the receptor, the $IC_{50}$ level was $1\times10^{-8}$M. The therapeutic window between tumor and nontarget cells is therefore 100 to 1000-fold. These reagents are highly potent and specifically toxic to brain tumor cells.

In Vivo Toxicity of Tfn-CRM107 Immunotoxins

To investigate the feasibility of intrathecal immunotoxin therapy for tumors in the cerebrospinal fluid, the toxicity of DT, CRM 107, and Tfn-CRM 107 was determined. The ability of human transferrin to bind to transferrin receptors from other species (unlike a monoclonal antibody to the human transferrin receptor) allows a comparison of toxicity in a number of species. Varying concentrations of the toxins were injected percutaneously into the cisterna magna of guinea pigs, rates and rhesus monkeys.

For guinea pigs, the maximum safe dose (maximum dose where no significant weight loss was observed) of DT was between $3.2\times10^{-11}$M to $3.2\times10^{-12}$M, as shown in Table V. Up to 100-fold higher doses of CRM 107 were tolerated without detectable toxicity. Therefore, in vivo toxicity of CRM 107 is about 1/100 of that of DT, while the nonspecific toxicity of CRM 107 in vitro is 1/10,000 that of DT. Furthermore, conjugation of CRM 107 Tfn reduced the toxicity approximately 10-fold more ($2\times10^{-9}$M). 454A12-CRM 107, which is incapable of binding to guinea pig transferrin receptors, could be injected at concentrations up to $1\times10^{-7}$M without toxicity. An identical concentration of 454A12-CRM 107 could be reached in the CSF of rates without toxicity.

Tfn-CRM 107 was injected intrathecally into the cisterna magna of adult Rhesus monkeys. Doses producing a CSF concentration of $3.3\times10^{-10}$M and $2\times10^{-9}$M were safely achieved. Neither dose of Tfn-CRM 107 caused apparent neurologic illness, and both animals were alive two months after treatment. Serum chemistry, liver enzymes, renal function, and hematologic parameters did not change. A CSF inflammatory response with pleocytosis, elevated protein, and normal glucose was apparent for 48 h, but had largely resolved by 14 days after treatment.

TABLE III

Sensitivity of Cell Lines Derived From Small Cell Carcinomas to CRM 107 and Ricin A chain Immunotoxins

| Cell Line | $IC_{50}$ 454A12-CRM107 |
|---|---|
| 417 | $2.0 \times 10^{-10}$M |
| 510 | $3.0 \times 10^{-9}$M |
| 209 | $2.0 \times 10^{-10}$M |

Cell lines derived from small cell carcinoma were incubated with the immunotoxin for 4 h followed by a 1 h pulse with $^{14}$[C]-leucine. Results are expressed as a percent of mock-treated controls.

TABLE IV $IC_{50}$ Values for Transferrin Receptor-Tageted Immunotoxins

| | $IC_{50}$ (M) | |
|---|---|---|
| | 454A12-CRM 107 | Tfn-CRM 107 |
| Medulloblasoma: Established: | | |
| TE671 | $2.6 \times 10^{-11}$ | $2.1 \times 10^{-12}$ |
| SNB 40 | $3.5 \times 10^{-11}$ | $3.9 \times 10^{-13}$ |
| Primary: | | |
| SNB 104 | nd | $2.5 \times 10^{-12}$ |
| SNB 105 | nd | $1.1 \times 10^{-10}$ |
| Glioblastoma | | |
| SNB 75 | $1.2 \times 10^{-10}$ | $6.5 \times 10^{-11}$ |
| SNB 101 | $3.8 \times 10^{-11}$ | $5.4 \times 10^{-12}$ |
| U251 | $1.6 \times 10^{-11}$ | $2.6 \times 10^{-12}$ |

TABLE IV-continued

IC$_{50}$ Values for Transferrin Receptor-Targeted Immunotoxins

| | IC$_{50}$ (M) | |
|---|---|---|
| | 454A12-CRM 107 | Tfn-CRM 107 |
| Breast Carcinoma | | |
| MCF-7 | $1.2 \times 10^{-10}$ | $2.3 \times 10^{-11}$ |
| T47D | $1.0 \times 10^{-10}$ | $1.1 \times 10^{-12}$ |
| ZR-75.1 | $2.1 \times 10^{-10}$ | $1.6 \times 10^{-11}$ |

A monoclonal antibody against the human transferrin receptor (454A12) was linked to CRM 107 and its efficacy compared with Tfn linked to CRM 107. Immunotoxins were incubated with the cells for 24 h followed by an incubation of 1 h with $^{14}$C-leucine. Cells were then harvested and concentrations of immunotoxin that inhibit protein synthesis by 50% of control values (IC$_{50}$) were determined.

TABLE V

Maximum Tolerated Dose in Guinea Pig CSF

| Toxin | Concentration |
|---|---|
| DT | $3.2 \times 10^{-11}$M – $3.2 \times 10^{-12}$M |
| CRM 107 | $3.2 \times 10^{-10}$M |
| Tfn-CRM 107 | $2.0 \times 10^{-9}$M |
| 454A12-CRM 107 | $1.0 \times 10^{-7}$M |

Toxin alone or toxin conjugates were injected percutaneously into the cisterna magna of strain 2 guinea pigs. The maximum dose permitting survival was determined. No significant weight loss was observed at these doses when compared with control animals.

The concentration of $2 \times 10^{-9}$M which was reached safely in vivo is 20–5000 times greater than the IC$_{50}$ of Tfn-CRM 107 to all the medulloblastoma, glioblastoma, or breast carcinoma cells assayed in culture. This comparison is illustrated in FIG. 6.

Inhibiting Effects of Circulating Anti-DT Antibodies

A critical factor in the efficacy of any CRM 107 immunotoxin in man is the level of inactivating anti-DT immunoglobulin produced by intentional immunization with diphtheria toxoid. Since CRM 107 differs in only one amino acid from DT, it is expected that the majority of circulating antibodies would be cross-reactive with CRM107. The effect of circulating levels of antibody in the serum was investigated, along with the effect of CSF on DT toxicity.

As shown in FIG. 8a, human sera may contain significant titers of inactivating antibody. Further titration of the sera with higher level of DT revealed approximately 10,000-fold block by sera. Two donors, reportedly not intentionally immunized against DT, exhibited dose-response curves that closely parallel the control DT curve, and serve as controls showing that human sera has no other effects of DT toxicity.

Low levels or total absence of inactivating antibody was found in the CSF (FIG. 8b) of normal volunteers. CSF from a glioblastoma patient, a patient with breast cancer-related leptomeningeal carcinomatosis, and one patient with lymphomatous leptomeningitis was also tested and showed no inhibition of DT toxicity. The fact that CSF has 0.2% to 0.4% of the IgG found in serum is consistent with the results found here. These results substantiate the belief that the CSF compartment is an immunologically priviliged site and demonstrate the potential for using CRM 107-based immunotoxins for the treatment of tumors within this compartment.

Of the immunotoxins described above, CRM 107 represents a significant advance in the design of toxins for use in immunotoxin therapy. CRM 107 is a genetically modified form of DT, differing from native DT at amino acid position 525. The toxin molecule consists of an A and B subunit. The A subunit enzymatically inactivates protein synthesis by transferring ADP ribose to elongation factor 2, thereby stopping the addition of amino acids to the growing polypeptide chain and thus killing the cell. The B subunit has two functions, facilitating both the binding of the toxin to the cell surface and the entry or translocation of the A subunit across the cell membrane into the cytosol where it functions. The advantage of CRM 107 is that the two amino acid changes in the toxin B chain inactivate toxin binding 8000-fold, yet have no effect on the translocation function. Therefore, by linking CRM 107 to a specific binding moiety such as a tumor-specific monoclonal antibody against the transferrin receptor, it is possible to target the full toxicity of the native toxin yet avoid the problems of non-specific toxicity caused by toxin binding.

The advantages of CRM 107-based immunotoxins become apparent when compared with immunotoxins made with DT A chains alone. Colomabatti et al., reported in J. Biol. Chem 261:3030–3035, 1986, compared the toxicity of native DT conjugated to the same antibody. A chain immunotoxins were found to be 10,000-fold less toxic than those made with native DT. This reduction in toxicity reflects the loss of the B chain translocation function. CRM 107 retains the translocation function, and therefore, when linked to a new binding site, maintains the full potency of killing found in the native toxin but with the high cell-type specificity of A chain conjugates.

Immunotoxins made with antibodies and whole toxins that are genetically altered in their binding domain possess several advantages over antibody-toxin A-chain conjugates. As previously mentioned, the B-chain translocation activity can be used in the absence of its binding function to increase reagent potency 10,000-fold over that of A-chain conjugates. Secondly, A-chain immunotoxins are constructed using a disulfide linkage. Reduction of the disulfide linkage leads to rapid loss of immunotoxin in vivo, and the release of free antibody that can bind cells and compete with intact immunotoxins. Use of whole toxins permits construction of non-cleavable thioether linkages between toxin and antibody. Thirdly, intact toxins are less susceptible to proteolytic inactivation than are toxin A fragments, and may survive longer in vivo.

Inactivating anti-DT immunoglobulin produced by intentional immunization with diphtheria toxoid presents a severe problem for the use of CRM-based immunotoxins systemmically. However, the CSF compartment represents an immunologically priviledged location where inactivation due to the presence of anti-DT immunoglobulin does not present a problem for the use of CRM-based immunotoxins. Similarly, the use of transferrin or an anti-transferrin receptor monoclonal antibody to target CRM 107 may be particularly efficacious in the CSF compartment. Expression of the transferrin receptor increases during cell replication in order to fulfill the dividing cell's need for iron. Since tumor cells are dividing while normal cells in the CNS parenchyma are quiescent, the transferrin receptor should provide an effective target for immunotoxin therapy. Therefore, CRM-based immunotoxins may be particularly efficacious for the treatment of primary brain tumors, metastatic brain tumors, CSF tumors, leptomeningeal leukemias and leptomeningeal carcinomatosis.

Representative cell lines derived from these types of tumors (medulloblastoma, glioblastoma, breast carcimoma, small cell carcimona) were used to assess the in vitro efficacy of an immunotoxin composed of a monoclonal antibody against the human transferring receptor linked to CRM 107. Medulloblastoma comprises 20% of all brain tumors in children. Because of the high incidence of recurrence and the propensity for dissemination through the cerebrospinal fluid, these children require postoperative radiation therapy which usually impairs their intellectual and physical development. A more targeted treatment such as immunotoxin therapy would be especially useful for this type of tumor. Intrathecal immunotoxin treatment of medulloblastoma has the added advantage of free access to the tumor cells within the cerebrospinal fluid, avoiding the potential problem of limited penetration into the tumor mass.

Glioblastomas, the most common primary malignant brain tumor, is rapidly fatal. The best treatment currently available, utilizing surgery, radiation therapy, and systemic chemotherapy, results in median survival times of less than one year. Inasmuch as most treatment failures occur because of local recurrence of glioma, immunotoxins administered directly into the cerebrospinal fluid or tumor, avoiding delivery problems caused by the blood-brain barrier, may provide additional tumor response and enhance log-kill required for effective treatment of glioblastoma.

A variety of carinomas, most commonly breast and lung, metastasize to the leptomeninges. The incidence of meningeal carcinomatosis in breast and lung cancer is believed to be rising because of improvements in the management of systemic disease. It is estimated that in a given year approximately 2,000 women have leptomeningeal carcinomatosis as a result of their primary breast cancer. The median survival after diagnosis with leptomeningeal carcinomatosis is 90 days. Less than 15% of patients are alive at 10 weeks after diagnosis. Without treatment, median survival is 4–6 weeks. Even in the best of hands, therapy for leptomeningeal carcinomatosis does not dramatically increase this survival time and does not act to cure any patients. Meningeal carcinomatosis is an attractive candidate for intrathecal immunotoxin therapy. Malignant cells grow as thin sheets bathed in cerebrospinal fluid and as a result problems involved with penetration of a solid tumor mass by immunotoxins are minimal.

Immunotoxins may be particularly efficacious for the treatment of neoplastic disease confined to compartments such as the peritoneum or intrathecal space. Direct delivery into the compartment avoids complications associated with systemic delivery and produces relatively high local concentrations, thereby achieving greater therapeutic effects.

Intrathecal administration, for purposes of this disclosure, includes intraventricular administration. Dosing may be accomplished by known means, including injection into the intrameningial space or via an indwelling catheter.

During surgery, following removal of intracranial tumors, the compositions of the invention can be administered directly into the cavity to prevent recurrence of tumor growth.

Suitable carriers are, for example, saline, or preferably, phosphate buffered saline. The compositions may, additionally, contain additives known in the art such as human albumin or other proteins or peptides.

The therapeutic potential for CRM 107 immunotoxins for these applications becomes apparent when one compares the in vitro efficacy and the in vivo toxicity. In rhesus monkeys, the highest dose of Tfn-CRM 107 tested ($2\times10^{-9}$M) was without toxicity. In guinea pigs, the maximum tolerated dose in the CSF was $2\times10^{-9}$M. The concentration of Tfn-CRM 107 required to kill 50% of the cells derived from medulloblastoma, glioblastoma, or breast carcinoma in vitro ranged from $1\times10^{-10}$M to $4\times10^{-13}$M. Therefore, it was possible to achieve a concentration of the conjugate in the CSF that is from 20- to 5000 -fold higher than that effective in vitro without detectable animal toxicity.

The CRM 107 conjugates of the present invention represent a significant advance in immunotoxin efficacy. They combine a high degree of tumor specificity, the ultimate degree of potency (one molecule per cell is sufficient to kill), with extremely rapid killing to produce a therapeutic window of up to 5000-fold. These factors, together with the advantages offered by compartmentalized treatment, demonstrate that CRM 107 immunotoxins have considerable potential for the treatment of leptomeningeal neoplasia.

The foregoing description of the specific embodiments will so fully reveal the general nature of the invention that others can, by applying current knowledge, readily modify and/or adapt for various applications such specific embodiments without departing from the generic concept, and therefore such adaptions and modifications are inteded to be comprehended within the meaning and range of equivalents of the disclosed embodiments.

We claim:

1. A method for treating primary or metastatic tumors located in the central nervous system or in a body compartment containing cerebrospinal fluid, comprising administering to a patient in an amount of an immunotoxin effective to kill cells of said tumors, wherein said immunotoxin comprises:

(a) a binding moiety which specifically binds to a cell surface receptor of a cell of a neural tumor, of a metastic small cell lung carcinoma, or of a metastatic breast carcinoma tumor, wherein said binding moiety is covalently linked to (b) a mutant diphtheria toxin, wherein said toxin consists of an A chain polypeptide and a B chain polypeptide, wherein said B chain polypeptide is inactivated as to membrane binding but retains full A chain translocating ability and contains at least one mutation selected from the group consisting of: a point mutation which changes serine residue 508 to another amino acid, a point mutation which changes serine residue 525 to another amino acid, and a point mutation which changes serine residue 508 to another amino acid together with a point mutation which changes proline residue 308 to another amino acid.

2. The method of claim 1, wherein said mutant diphtheria toxin contains one or two mutations selected from the group consisting of: a point mutation which changes serine residue 508 to phenylalanine, a point mutation which changes serine residue 525 to phenylalanine, and a point mutation which changes serine residue 508 to phenylalanine together with a point mutation which changes proline residue 308 to serine.

3. The method of claim 1, wherein said binding moiety binds to a cell surface receptor on a glioblastoma or medulloblastoma cell.

4. The method of claim 1, wherein said cell surface receptor is a transferrin receptor.

5. The method of claim 1, wherein said binding moiety is transferrin or a monoclonal antibody which specifically binds to a transferrin receptor.

6. The method of claim 5, wherein said binding moiety is transferrin.

7. The method of claim 5, wherein said binding moiety is a monoclonal antibody which specifically binds to a transferrin receptor.

8. The method of claim 1, wherein said tumor is a neurologic tumor of the central nervous system.

9. The method of claim 1, wherein said tumor is glioblastoma or medulloblastoma.

10. The method of claim 1, wherein said tumor is a metastatic tumor of breast carcinoma origin or is a metastatic tumor of small cell lung carcinoma origin.

11. The method of claim 1, wherein said immunotoxin is administered to a body compartment containing cerebrospinal fluid.

12. The method of claim 1, wherein said immunotoxin is administered intrathecally, intraventricularly, or to a cavity left by surgical resection of said tumor.

* * * * *

UNITED STATES PATENT AND TRADEMARK OFFICE
CERTIFICATE OF CORRECTION

PATENT NO.  : 5,728,383

DATED  : March 17, 1998

INVENTOR(S)  : Johnson et al.

It is certified that error appears in the above-identified patent and that said Letters Patent is hereby corrected as shown below:

Column 6, line 32, "$^{12}C$" should be --$^{14}C$--;

Column 10, line 24, "CHT1" should be --UCHT1--;

Column 14, line 6, "rates" should be --rats--;

Column 14, line 20, "rates" should be --rats--;

Column 18, line 24, "patient in an amount" should be --patient an amount--.

Signed and Sealed this

Thirty-first Day of August, 1999

Attest:

Q. TODD DICKINSON

*Attesting Officer*  *Acting Commissioner of Patents and Trademarks*